(12) United States Patent
Lay et al.

(10) Patent No.: US 12,109,406 B2
(45) Date of Patent: *Oct. 8, 2024

(54) CONDUCTIVE CIRCUIT

(71) Applicant: Caldera Medical, Inc., Westlake Village, CA (US)

(72) Inventors: Graham Lay, Galway (IE); Will Moranvil, Galway (IE); Paul Monahan, Galway (IE); Robin Crossley, Windsor (GB); Andrea Potter, Windsor (GB); Ruth Maher, Brazelton, GA (US)

(73) Assignee: Caldera Medical, Inc., Westlake Village, CA (US)

( * ) Notice: Subject to any disclaimer, the term of this patent is extended or adjusted under 35 U.S.C. 154(b) by 397 days.

This patent is subject to a terminal disclaimer.

(21) Appl. No.: 17/614,122

(22) PCT Filed: May 28, 2020

(86) PCT No.: PCT/EP2020/064912
§ 371 (c)(1),
(2) Date: Nov. 24, 2021

(87) PCT Pub. No.: WO2020/239950
PCT Pub. Date: Dec. 3, 2020

(65) Prior Publication Data
US 2022/0152380 A1 May 19, 2022

(30) Foreign Application Priority Data

May 28, 2019 (GB) .................................... 1907517
May 28, 2019 (GB) .................................... 1907520
Jun. 19, 2019 (GB) .................................... 1908771

(51) Int. Cl.
*A61N 1/04* (2006.01)
*A61N 1/36* (2006.01)

(52) U.S. Cl.
CPC ....... *A61N 1/0484* (2013.01); *A61N 1/36007* (2013.01); *A61N 1/36014* (2013.01)

(58) Field of Classification Search
CPC .............. A61N 1/0484; A61N 1/36007; A61N 1/36014; A61N 1/0452; A41D 13/1281; A61B 5/0205; A61B 5/256; A61B 5/296
See application file for complete search history.

(56) References Cited

U.S. PATENT DOCUMENTS 6,944,503 B2    9/2005   Crowe
7,504,550 B2    3/2009   Tippey
(Continued)

FOREIGN PATENT DOCUMENTS

GB      2555592       5/2018
JP      2001057967    3/2001
(Continued)

OTHER PUBLICATIONS

Choosing the Best Prolapse Support Garment, posted Jan. 7, 2019 [online], (retrieved Jun. 21, 2022). Retrieved from the internet, https://www.femicushion.com/blogs/femicushion/how-to-choose-the-right-prolapse-support-garment (Year: 2019).
(Continued)

*Primary Examiner* — Catherine M Voorhees
(74) *Attorney, Agent, or Firm* — Inskeep IP Group, Inc.

(57) ABSTRACT

In general terms, the invention provides a circuit for delivering an electromagnetic signal to a human or animal body via contact with the skin of the body. The circuit comprises a plurality of printed layers provided on a base. The plurality of printed layers includes a first printed layer, and a second printed layer having a portion that overlays the first printed layer and a portion that overhangs the first printed layer.

(Continued)

Optionally the portion that overhangs the first printed layer contacts the base or another of the printed layers of the plurality of printed layers.

19 Claims, 10 Drawing Sheets

(56) References Cited

U.S. PATENT DOCUMENTS

| | | | |
|---|---|---|---|
| 8,494,658 | B2 | 7/2013 | Crowe |
| 8,739,397 | B2 | 6/2014 | Nagata |
| 9,386,684 | B2 | 7/2016 | Sime |
| 9,545,514 | B2 | 1/2017 | Minogue |
| 9,675,802 | B2 | 6/2017 | Crowe |
| D847,457 | S | 5/2019 | Piombino |
| 10,315,402 | B2 * | 6/2019 | Brook .................. B44C 1/1733 |
| D864,523 | S | 10/2019 | Diamond |
| D917,127 | S | 4/2021 | Chisholm |
| D922,730 | S | 6/2021 | Bae |
| D939,189 | S | 12/2021 | De Mulder |
| D953,694 | S | 6/2022 | Zhang |
| 11,839,756 | B2 * | 12/2023 | Lay ...................... A61N 1/0452 |
| 2002/0077688 | A1 | 6/2002 | Kirkland |
| 2002/0099277 | A1 * | 7/2002 | Harry .................. A61B 5/6831 |
| | | | 600/301 |
| 2005/0159028 | A1 * | 7/2005 | Sweetland ............... H01R 4/58 |
| | | | 439/67 |
| 2013/0060115 | A1 | 3/2013 | Gehman |
| 2013/0248226 | A1 * | 9/2013 | Sime ...................... H05K 1/038 |
| | | | 156/247 |
| 2015/0040282 | A1 | 2/2015 | Longinotti-Buitoni |
| 2015/0366504 | A1 * | 12/2015 | Connor ................ A61B 5/6804 |
| | | | 600/301 |
| 2016/0374615 | A1 | 12/2016 | Tsukada |
| 2017/0182320 | A1 | 6/2017 | Kolb |
| 2018/0021184 | A1 * | 1/2018 | Monson ............... H01Q 9/0457 |
| | | | 340/573.5 |
| 2019/0132948 | A1 | 5/2019 | Longinotti-Buitoni |
| 2020/0353239 | A1 | 11/2020 | Daniels |
| 2020/0360681 | A1 | 11/2020 | Lay |
| 2021/0100681 | A1 | 4/2021 | Miles |
| 2021/0298369 | A1 | 9/2021 | Polstein |
| 2022/0152380 | A1 | 5/2022 | Lay |

FOREIGN PATENT DOCUMENTS

| | | |
|---|---|---|
| JP | 2003250914 | 9/2003 |
| JP | 2010502251 | 1/2010 |
| JP | 2010220754 | 10/2010 |
| WO | 2003006106 | 1/2003 |
| WO | 2007138071 | 12/2007 |
| WO | 2008088985 | 7/2008 |
| WO | 2012116407 | 9/2012 |
| WO | 2017075703 | 5/2017 |
| WO | 2018055207 | 3/2018 |
| WO | 2018098046 | 5/2018 |
| WO | 2019110595 | 6/2019 |

OTHER PUBLICATIONS

In Novo Kegel Exerciser, posted NA [online], (retrieved Jun. 21, 2022). Retrieved from the internet, https://www.myinnovo.com/products/innovo-starter-kit (Year: NA).

Vulvar Varicosity and Prolapse, reviewed Jun. 21, 2021 posted NA [online], (retrieved Jun. 21, 2022). Retrieved from the internet,https://www.underworks.com/vulvar-varicosity-and-prolapse-support-brief-with-g roi n-compression-bands-with-hot-cold-therapy-gel-pad?gclid=EAlalQobChMI_M-cuPO--AlVhfLjBx3EzwHSEAkY (Year: 2021).

Description of INNOVOR shorts, <https://www.myinnovo.com/uk/healthcare-professionals/clinical- studies/innovo-strengthens-the-entire-pelvic-floor-musculature/>, dated Jan. 21, accessed Nov. 25, 2019, 4 pages.

International Search Report and Written Opinion, International Patent Application No. PCT/EP2020/064912, Dec. 9, 2020, 20 pages.

Screenshot—The INNOVO Story with Dr. Ruth Maher & Dr. Sherry Ross, INNOVO, <https://www.youtube.com/watch?v=Pm6rAOwnPBo>, uploaded May 30, 2019; see especially 2:09, 1 page.

Search Report, British Application No. GB1907517.5, dated Nov. 22, 2019, 1 page.

Search Report, British Application No. GB1908771.7, dated Nov. 29, 2019, 1 page.

* cited by examiner

CONDUCTIVE CIRCUIT

TECHNICAL FIELD

This invention relates to a conductive circuit for delivering electrical impulses to a human or animal body, particularly such a conductive circuit for use on or in garments.

BACKGROUND

It is known in the prior art to use external electric stimulation to improve muscle condition. Such devices are described in, for example WO03006106. The use of such devices may be to develop muscle tone, either for cosmetic purposes or for the treatment of medical conditions. One condition for which treatment of this nature may be effective is incontinence, as described in WO2007138071. In such devices, targeted impulses are sent via conductive pads producing over 180 contractions per session. The pelvic floor muscles are contracted, improving muscle strength and control, directly targeting a primary cause of stress urinary incontinence. It is currently estimated that over 5 million women in the UK experience the symptoms of urinary incontinence and of these, half of all sufferers aged between 18 and 65 years of age are moderately or greatly bothered by it. About one third of women experience urinary incontinence after giving birth, and over 65% of these women are still affected by it 12 years later. 23% of women with urinary incontinence say that it reduces their activity level; 23% state that it adversely affects their sex life; and 31% dress differently because of their symptoms. Whilst pelvic floor disorders mainly affect women, they can also affect men.

It is important that the impulses are correctly delivered, to target the correct muscles. Durability of devices for delivering the impulses, and in particular durability of conductive circuits within such devices, is a key factor in ensuring such correct delivery.

SUMMARY OF THE INVENTION

In general terms, an aspect of the invention provides a circuit for delivering an electromagnetic signal to a human or animal body via contact with the skin of the body. The circuit comprises a plurality of printed layers provided on a base. The plurality of printed layers includes a first printed layer, and a second printed layer having a portion that overlays the first printed layer and a portion that overhangs the first printed layer. Optionally the portion that overhangs the first printed layer contacts the base or another of the printed layers of the plurality of printed layers.

Thus, a first aspect of the present invention provides a conductive circuit comprising one or more electrodes for delivering an electromagnetic signal to a human or animal body, the conductive circuit comprising a base and a plurality of printed layers supported by the base, the plurality of printed layers including a first printed non-conductive layer at least partially defined by a first perimeter edge, and a second printed non-conductive layer at least partially defined by a second perimeter edge and overlaying the first printed non-conductive layer, wherein at least a portion of the second perimeter edge is offset from the first perimeter edge such that the second printed non-conductive layer overhangs the first printed non-conductive layer.

In this way, an improved conductive circuit is achieved. In particular, the conductive circuit is more durable than existing circuits. A key role of the first and second printed non-conductive layers is to overlay, or encapsulate, conductive elements of the circuit that carry electromagnetic signals. It is therefore important that these layers remain in situ during the service life of any item to which the circuit is applied.

The overhang of the outer second printed non-conductive layer beyond the inner first printed non-conductive layer provides a particularly robust and durable arrangement which resists peel of those layers in service. This is at least in part because load transfer across the first and second perimeter edges is improved. Particularly in applications in which the base is flexible or stretchable, the application of the plurality of printed layers to the base can alter the modulus of elasticity of the base in the regions to which they are applied, resulting in high loads at the edges of the printed layers in particular. The overhang arrangement of the present invention acts to better distribute such loads and avoid unwanted peel of the non-conductive layers in use.

The second printed layer overhangs the first printed layer such that a portion of the second printed non-conductive layer defined by the second perimeter edge protrudes beyond, or projects beyond, the first perimeter edge of the first printed non-conductive layer.

The conductive circuit is primarily intended for use in garments for humans, though other uses are possible.

In an embodiment, the base is a support for the plurality of printed layers. The base may be any appropriate structure, for example it may also be a layer. In one embodiment, the base is a fabric, particularly a stretch fabric. A stretch fabric is any fabric that may be reversibly stretched in at least one direction. Stretch fabrics include, for example, fabrics comprising elastane. The fabric may, for example, be a fabric comprising a polyamide or a polyurethane.

Each of the printed layers, including the first and second printed non-conductive layers, comprises a layer formed by printing an ink layer by an appropriate method, including, but not limited to screen printing, reel-to-reel printing, dot matrix printing, laser printing, cylinder press printing, ink jet printing, flexographic printing, lithographic printing, offset printing, digital printing, gravure printing or xerographic printing. The ink may be printed directly onto the base, or alternatively may be first printed onto a transfer substrate, and subsequently transferred onto the base by a transfer process.

The first and second non-conductive printed layers may comprise a non-conductive material, i.e. a material that has a high electrical resistivity. The non-conductive material may comprise any appropriate material, such as a printable ink. Thus, the first and second non-conductive printed layers may each comprise one or more non-conductive ink layers. An appropriate ink may comprise a water-based printing ink, an ultraviolet-cured printing ink, a solvent based ink, or a latex printing ink, for example. A particularly preferred ink for the non-conductive layers comprises a screen-printable ink of CMYK toner.

The first and second printed non-conductive layers (optionally the plurality of printed layers) may have a higher modulus of elasticity than the base. Thus, resistance to stretching of the base is higher in regions of the base in which the first and second printed non-conductive layers are applied than in other regions of the base. This results in high concentrations of loads at the edges of regions in which the first and second printed non-conductive layers are applied, for example at the edges of exposed regions of printed conductive layers defined by the second perimeter edge. The overhang of the second printed non-conductive layer mitigates the effects of such loads, and thereby reduces the risk of peeling of the first and second printed non-conductive layers in use.

The plurality of printed layers preferably comprises a printed conductive layer partially overlaid by the first and second printed non-conductive layers, and the second perimeter edge preferably defines one or more exposed regions of the conductive circuit in which the printed conductive layer is not overlaid by the first and second printed non-conductive layers. That is, the second perimeter edge may define one or more terminal edges of the second printed non-conductive layer that define one or more boundaries of the one or more exposed regions. In this way, the overhang of the second printed non-conductive layer serves to prevent peeling of the first and second printed non-conductive layers away from the conductive layer.

The conductive layer is a printed conductive layer. It may comprise a conductive ink. The conductive ink may be any appropriate conductive ink, such as, but not limited to, an ink comprising silver, silver chloride, carbon or copper.

The conductive layer may be applied directly to the base, or further layers may be applied between the conductive layer and the base. For example, one or more further non-conductive printed layers may be provided between the conductive layer and the base. In one embodiment, the electrode further comprises an adhesive layer. The adhesive layer may be applied between the base and the conductive layer, optionally between the base and the one or more further non-conductive printed layers. It may be applied by any appropriate means, including printing.

The second printed non-conductive layer may comprise an outermost layer of the conductive circuit. Thus, the second printed non-conductive layer may be configured to contact the skin of a human or animal body in use.

The plurality of printed layers may further include at least one printed conductive layer supported by the base and partially overlaid by the first and second printed non-conductive layers to define one or more exposed regions of the one or more electrodes in which the at least one printed conductive layer is exposed to thereby be configured to contact the skin of a human or animal body in use. Thus, the one or more exposed regions are each a portion of an electrode via which electromagnetic signals can be transferred to a human or animal body, via contact with its skin.

The conductive layer is a printed conductive layer. It may comprise a conductive ink. The conductive ink may be any appropriate conductive ink, such as, but not limited to, an ink comprising silver, silver chloride, carbon or copper.

The conductive layer may be applied directly to the base, or further layers may be applied between the conductive layer and the base. For example, one or more further non-conductive printed layers may be provided between the conductive layer and the base. In one embodiment, the electrode further comprises an adhesive layer. The adhesive layer may be applied between the base and the conductive layer, optionally between the base and the one or more further non-conductive printed layers. It may be applied by any appropriate means, including printing.

The one or more exposed regions of the one or more electrodes may be defined at least partially by the second perimeter edge. That is, the second perimeter edge may define one or more terminal edges of the second printed non-conductive layer that define one or more boundaries of the one or more exposed regions. Thus, the overhang of the second printed non-conductive layer may serve to prevent peeling of the first and second printed non-conductive layers away from the one or more exposed regions.

The conductive circuit may further comprise one or more connection tracks, each connection track providing an electrically conductive path between a respective one of the one or more electrodes and an electrical contact configured to enable connection to a controller arranged to supply an electromagnetic signal to the one or more electrodes. The one or more connection tracks may be defined by the plurality of printed layers.

In some embodiments the first perimeter edge and/or the second perimeter edge are offset from an interface between each of the one or more connection tracks and a respective one of the one or more electrodes. In this way, load concentrations associated with the first and second perimeter edges are separated from load concentrations associated with the interface, leading to increased durability of the circuit. Preferably, the first perimeter edge and/or the second perimeter edge are offset from the interface by a distance greater than the offset between the first and second perimeter edges.

The interface between each of the one or more connection tracks and a respective one of the one or more electrodes may comprise a region in which a cross-sectional area of the conductive circuit changes. For example, an overall width of the conductive circuit may change (for example, the conductive circuit may be wider in electrode regions than in track regions), and/or a thickness of the conductive circuit may change (for example, the conductive circuit may have a higher thickness in some regions, such as the tracks, to increase the modulus of elasticity (resistance to stretching) in those regions). Such changes of cross-sectional area may result in load concentrations at the interface.

The interface between each of the one or more connection tracks and a respective one of the one or more electrodes may comprise a region in which a modulus of elasticity of the conductive circuit changes. For example, a change in the cross-sectional area of the conductive circuit in the region of the interface may result in such a change in the modulus of elasticity. The one or more tracks may each have a lower modulus of elasticity than a respective one of the one or more electrodes. Such a change in modulus may result in load concentrations at the interface.

The plurality of printed layers preferably comprises a printed conductive layer of the one or more connection tracks, the printed conductive layer of each of the one or more connection tracks being electrically connected to a respective one of the one or more electrodes. The printed conductive layer of each of the one or more connection tracks is preferably electrically connected to (most preferably contiguous with) a printed conductive layer of a respective one of the one or more electrodes. The first and second printed non-conductive layers preferably overlay the printed conductive layer of each of the one or more connection tracks to thereby encapsulate at least a majority of the printed conductive layer.

In some embodiments the or each electrical contact comprises an exposed region of the respective connection track in which the printed conductive layer of the connection track is not overlaid by the first and second printed non-conductive layers, and wherein the exposed region is defined by the second perimeter edge. That is, the second perimeter edge may define one or more terminal edges of the second printed non-conductive layer that define one or more boundaries of the exposed region. Thus, the overhang of the second printed non-conductive layer may serve to prevent peeling of the first and second printed non-conductive layers away from the exposed region.

The plurality of printed layers may further comprise one or more further printed non-conductive layers between a printed conductive layer and the base. The one or more further printed non-conductive layers thus may serve to electrically isolate the printed conductive layer from the base.

The first and second printed non-conductive layers may each have a thickness of about 0.1 mm or less, optionally about 0.05 mm or less. In some embodiments the second perimeter edge is offset from the first perimeter edge by about 0.5 mm or more, optionally about 2 mm or less. In general terms, the second perimeter edge may be offset from the first perimeter edge by a distance of at least 10 times a thickness of the first printed layer, optionally at least 20 times, at least 30 times, at least 40 times, or at least 50 times.

In general terms, a further aspect of the invention provides a circuit for delivering an electromagnetic signal to a human or animal body via contact with the skin of the body. The circuit comprises a plurality of printed layers provided on a base, the plurality of printed layers including a first printed conductive layer forming an electrode of the circuit and a second printed conductive layer forming a track of the circuit, the first and second printed conductive layers being electrically isolated from one another by a non-conductive layer of the plurality of printed layers where the first and second printed conductive layers overlap.

Thus, a second aspect of the invention provides a conductive circuit comprising: one or more electrical contacts for connection to a controller arranged to supply an electromagnetic signal; one or more electrodes for delivering the electromagnetic signal to a human or animal body; and one or more tracks, each track providing an electrically conductive path between a respective one of the one or more electrodes and the one or more electrical contacts, wherein the conductive circuit comprises a base and a plurality of printed layers supported by the base, the plurality of printed layers including: a first conductive printed layer having at least one exposed region in which the first conductive printed layer is exposed to contact the skin of a human or animal body in use, the at least one exposed region forming one of the one or more electrodes; a second conductive printed layer sandwiched between the at least one exposed region and the base to form the one or more tracks; and a non-conductive insulating printed layer between the first and second conductive printed layers to electrically isolate the first conductive printed layer from the second conductive printed layer.

This arrangement protects the tracks from stretching in the region in which they coincide with the exposed region forming the electrode. This is particularly useful because stretching of the conductive layers causes undesirable changes in the electrical conductivity of the tracks which may affect the delivery of therapeutic electromagnetic signals.

A further benefit is in minimising the overall length of the tracks, since the tracks can overlap with the electrode instead of tracking around it. This in turn minimises the overall amount of conductive material in the circuit, resulting in a lower overall material cost.

The conductive circuit is primarily intended for use in garments for humans, though other uses are possible.

An elastic modulus of the plurality of printed layers may be higher than an elastic modulus of the base. Thus, resistance to stretching of the base is higher in regions of the base in which the plurality of printed layers are provided than in other regions of the base. Similarly, an elastic modulus of the conductive circuit may be higher in regions in which the plurality of printed layers are provided than in regions in which the plurality of printed layers are not provided. For example, the elastic modulus of the conductive circuit may be highest at the one or more electrodes and lowest at regions where there are no printed layers provided on the base.

In such arrangements higher modulus regions protect features of the circuit such as the one or more electrodes from stretching, while lower modulus regions serve to enable stretching of the base to provide a close fit between the skin and the electrodes. The invention of the second aspect maximises such lower modulus regions by minimising the need for tracks to pass through the spaces between and adjacent to the one or more electrodes, and thus minimising the need for printed layers in those spaces.

The base may be any appropriate structure, for example it may also be a layer. In one embodiment, the base is a fabric, particularly a stretch fabric. A stretch fabric is any fabric that may be reversibly stretched in at least one direction. Stretch fabrics include, for example, fabrics comprising elastane. The fabric may, for example, be a fabric comprising a polyamide or a polyurethane.

The first conductive printed layer optionally forms a respective one of the one or more connection tracks that provides an electrical connection between the at least one exposed region of the first conductive printed layer and a respective one of the electrical contacts. In this way, the first conductive printed layer forms a first one of the one or more electrodes and its associated connection track (and optionally its associated electrical contact).

In addition, or alternatively, the second conductive printed layer optionally has at least one exposed region in which the second conductive printed layer is exposed to contact the skin of a human or animal body in use, the at least one exposed region forming another of the one or more electrodes. Thus, the second conductive printed layer forms another of the one or more electrodes and its associated connection track (and optionally its associated electrical contact).

The first and second conductive printed layers may each comprise a conductive material, optionally the same conductive material. In some embodiments the first conductive printed layer may comprise a first conductive material, the second conductive printed layer may comprise a second conductive material, and the first material may be different to the second material.

In some embodiments the first and second conductive printed layers may have substantially the same thickness. In other embodiments the first conductive layer may have a different thickness to the second conductive layer.

Each of the printed layers, including the first and second conductive printed layers and the non-conductive insulating printed layer, comprises a layer formed by printing an ink layer by an appropriate method, including, but not limited to screen printing, reel-to-reel printing, dot matrix printing, laser printing, cylinder press printing, ink jet printing, flexographic printing, lithographic printing, offset printing, digital printing, gravure printing or xerographic printing. The ink may be printed directly onto the base, or alternatively may be first printed onto a transfer substrate, and subsequently transferred onto the base by a transfer process.

The non-conductive insulating printed layer may comprise a non-conductive material, i.e. a material that has a high electrical resistivity. The non-conductive material may comprise any appropriate material, such as a printable ink. Thus, the non-conductive printed insulating layer may comprise one or more non-conductive ink layers. An appropriate ink may comprise a water-based printing ink, an ultraviolet-cured printing ink, a solvent based ink, or a latex printing ink, for example. A particularly preferred ink for the non-conductive layer comprises a screen-printable ink of CMYK toner.

The first and second conductive layers are printed conductive layers. They may comprise a conductive ink. The conductive ink may be any appropriate conductive ink, such as, but not limited to, an ink comprising silver, silver chloride, carbon or copper.

The second conductive printed layer may be directly adjacent the base, or the plurality of printed layers may include one or more further layers between the second conductive layer and the base. For example, the plurality of printed layers may include one or more further non-conductive printed layers between the second conductive layer and the base.

In one embodiment, the conductive circuit further comprises an adhesive layer. The adhesive layer may be applied between the base and the plurality of printed layers, optionally between the base and the one or more further non-conductive printed layers. It may be applied by any appropriate means, including printing.

The plurality of printed layers may include an outermost encapsulating printed non-conductive layer laminated over the first printed conductive layer. The outermost encapsulating printed non-conductive layer may have an opening defining the at least one exposed region of the first printed conductive layer.

The circuit of the first or second aspects may comprise a connector configured to provide an electrical connection between the one or more electrodes and a power supply, controller, or control unit. The connector is preferably electrically connected to the one or more electrical contacts.

The invention extends to conductive circuits comprising features of both the first and second aspects.

A third aspect of the invention provides a kit of parts for providing a conductive circuit according to the first and/or second aspects, comprising a base, and a substrate carrying the plurality of printed layers, the substrate being configured to enable transfer of the plurality of printed layers onto the base by a transfer process to provide the conductive circuit.

The kit may comprise a layer of adhesive on the plurality of printed layers, the layer of adhesive being configured to adhere the plurality of printed layers to the base during the transfer process.

Similarly, a related aspect provides a kit comprising a conductive circuit according to the first and/or aspects and a power supply, control unit and/or controller for providing an electromagnetic signal to the one or more electrodes of the conductive circuit.

A fourth aspect of the invention provides a wearable garment comprising one or more conductive circuits according to the first and/or second aspects.

The garment may comprise more than one electrode, for example, it may comprise two, three, four, five, six, seven, eight or more electrodes. The garment may comprise one or more electrodes with one or more conductive regions. For example, the garment may comprise at least two, three, four, five, six, seven, eight, nine, ten or more conductive regions. In use, the electromagnetic signal may pass from one electrode to another, and/or from one or more electrodes of one conductive circuit to one or more electrodes of another conductive circuit.

The electrode may be applied to the garment, or fabric of the garment may form the base of the electrode.

In an embodiment, the garment is for the lower body. For example, the garment may be trousers or shorts. When the garment is for the lower body, the conductive regions may be provided, for example, on the calves, thighs and/or buttocks.

A related fifth aspect of the invention thus provides a garment for wearing on the lower body of a wearer, the garment including one or more electrodes for delivering an electromagnetic signal to the wearer via contact with the skin of the wearer, the one or more electrodes comprising a pair of gluteal electrodes positioned according to one or more positional rules. The positional rules preferably comprise one or more of the following:

A horizontal offset between the inter-gluteal cleft of a wearer of the garment and a nearest side edge of the gluteal electrode of about between 12 mm and 20 mm, optionally about 17 or 18 mm, e.g. 17.5 mm;

A horizontal offset between nearest side edges of the pair of gluteal electrodes at their closest points of between 30 mm and 40 mm, optionally about 35 mm; and/or A vertical offset between the natural waist of a wearer of the garment 100 and an uppermost (nearest) edge of the gluteal electrode of at least 75 mm, optionally at least 70 mm.

The natural waist may be in some circumstances defined at a position approximately 100 mm offset vertically upwards from the point of a wearer's hip, i.e. the anterior bony protrusion of the hip that can usually be felt under the skin, sometimes referred to as the anterior superior iliac spine. Thus, the uppermost edge of the gluteal electrode may be located relative to the point of a wearer's hip such that it is no more than 25 mm vertically offset above the point of a wearer's hip.

A particular benefit of the above positional rules is in ensuring correct placement of the gluteal electrodes across multiple garment sizes, to ensure effective therapeutic effect in each of those garment sizes.

By 'edge' is meant an edge of the active area of the electrode, i.e. an edge of an exposed region of the electrode in which the conductive material is exposed to contact the wearer's skin in use.

The anatomical features referred to may have known relationships to specific features of the garment. For example, the inter-gluteal cleft of the wearer may correspond to a generally vertical seam of the garment (or an alternative feature of a panel of the garment) that aligns with the inter-gluteal cleft of the wearer in use. Thus, the horizontal offset of each gluteal electrode may be defined relative to such a feature of the garment. For example, the nearest side edge of each gluteal electrode may be offset horizontally from a nominal line bisecting left and right rear regions of the garment by about 17 or 18 mm, e.g. 17.5 mm, optionally between 15 mm and 20 mm.

Similarly, the natural waist of the wearer may have a known positional relationship with, for example be aligned with, a feature of a waistband of the garment, such as a horizontal seam of the waistband. The point of hip may also have a known positional relationship with a feature of a waistband of the garment, such as a horizontal seam of the waistband. Thus, the vertical offset of each gluteal electrode may be defined relative to such a feature of the garment. For example, the uppermost (nearest) edge of the gluteal electrode may be vertically offset from a feature of a waistband of the garment (preferably a generally horizontal seam of the waistband of the garment) by at least 75 mm, optionally at least 70 mm, wherein the feature of the waistband is configured to be aligned with the natural waist of a wearer in use.

In particularly preferred embodiments the one or more electrodes further comprise a pair of hip electrodes, each hip electrode being positioned such that an uppermost edge of the hip electrode is higher than an uppermost edge of the pair of gluteal electrodes.

In one such embodiment, the conductive regions are provided on the thighs, particularly the back and sides of the thighs and buttocks. The garment may comprise two conductive circuits, a first conductive circuit having one or more electrodes or conductive regions for the left side of the body, and a second conductive circuit having a corresponding one or more electrodes or conductive regions for the right side of the body. There are preferably no seams that dissect either the left or right conductive circuit. The garment may further comprise a left panel carrying the first conductive circuit and a right panel carrying the second conductive circuit. The left and right panels preferably encircle the left and right thighs, respectively, in use. The left and right panels are preferably joined to one another by one or more seams in the crotch and/or inner thigh region. There are preferably no further panels or seams in the outer thigh or buttocks region.

A related sixth aspect of the invention comprises a plurality of garments for wearing on the lower body of a wearer, each garment including one or more electrodes for delivering an electromagnetic signal to the wearer via contact with the skin of the wearer, and in each garment the one or more electrodes comprising a pair of gluteal electrodes, wherein each garment is a different size (i.e. each has dimensions corresponding to a respective garment size from a plurality of garment sizes, each garment size being for a particular size or shape of wearer), and in each garment each gluteal electrode is positioned according to one or more common positional rules. The one or more common positional rules preferably include:

A horizontal offset between the inter-gluteal cleft of a wearer of the garment 100 and a nearest side edge of the gluteal electrode of about between 12 mm and 20 mm, optionally about 17 or 18 mm, e.g. 17.5 mm;

A horizontal offset between nearest side edges of the pair of gluteal electrodes at their closest points of between 30 mm and 40 mm, optionally about 35 mm; and/or A vertical offset between the natural waist of a wearer of the garment 100 and an uppermost (nearest) edge of the gluteal electrode of at least 75 mm, optionally at least 70 mm.

The natural waist may be in some circumstances defined at a position approximately 100 mm offset vertically upwards from the point of a wearer's hip, i.e. the anterior bony protrusion of the hip that can usually be felt under the skin, sometimes referred to as the anterior superior iliac spine. Thus, the uppermost edge of the gluteal electrode may be located relative to the point of a wearer's hip such that it is no more than 25 mm vertically offset above the point of a wearer's hip.

A particular benefit of the above positional rules is in ensuring correct placement of the gluteal electrodes across the multiple garment sizes, to ensure effective therapeutic effect in each of those garment sizes. The term 'different size' is used here to refer to different garment sizes for fitting different sizes of wearer. For example, the sizes may each correspond to a size within a standard garment sizing system.

By 'edge' is meant an edge of the active area of the electrode, i.e. an edge of an exposed region of the electrode in which the conductive material is exposed to contact the wearer's skin in use.

The anatomical features referred to may have known relationships to specific features of the garment. For example, the inter-gluteal cleft of the wearer may correspond to a generally vertical seam of the garment (or an alternative feature of a panel of the garment) that aligns with the inter-gluteal cleft of the wearer in use. Thus, the horizontal offset of each gluteal electrode may be defined relative to such a feature of the garment. For example, the nearest side edge of each gluteal electrode may be offset horizontally from a nominal line bisecting left and right rear regions of the garment by about 17 or 18 mm, e.g. 17.5 mm, optionally between 15 mm and 20 mm.

Similarly, the natural waist of the wearer may have a known positional relationship with, for example be aligned with, a feature of a waistband of the garment, such as a horizontal seam of the waistband. The point of hip may also have a known positional relationship with a feature of a waistband of the garment, such as a horizontal seam of the waistband. Thus, the vertical offset of each gluteal electrode may be defined relative to such a feature of the garment. For example, the uppermost (nearest) edge of the gluteal electrode may be vertically offset from a feature of a waistband of the garment (preferably a generally horizontal seam of the waistband of the garment) by at least 75 mm, optionally at least 70 mm, wherein the feature of the waistband is configured to be aligned with the natural waist of a wearer in use. In particularly preferred embodiments the one or more electrodes further comprise a pair of hip electrodes, each hip electrode being positioned such that an uppermost edge of the hip electrode is higher than an uppermost edge of the pair of gluteal electrodes.

In the fifth and sixth aspects the one or more electrodes may be provided in a circuit configured according to the first or second aspects, or in any other form disclosed herein. In particular, the circuits may each comprise a plurality of printed layers provided on a fabric base of the garment or garments, the plurality of printed layers including at least one printed conductive layer forming the one or more electrodes. The plurality of printed layers may further include one or more printed non-conductive layers. The one or more printed non-conductive layers may overlay the at least one printed conductive layer, and may in addition comprise one or more apertures to define one or more exposed regions of the printed conductive layer forming the one or more electrodes.

Alternatively, the garment is for the upper body or for the limbs.

In an embodiment, the conductive circuits (comprising conductive regions) are provided on both sides of the garment, so that the conductive circuits (regions) are positioned on both the left and right sides of the body when in use. The conductive circuits (conductive regions) may arranged so as to be substantially symmetrical about the mid-sagittal plane of the human body when in use.

The garment or garments may further comprise a power supply, control unit and/or controller for providing an electromagnetic signal to the one or more electrodes of the one or more conductive circuits. The power supply and control unit and/or controller may be provided as an integrated unit.

The garment or garments may further comprise one or more sensors, for example to provide information about the user of the garment. Examples of sensors include an accelerometer, to provide information about the position of the user when using the garment; a thermometer; a sensor to detect muscle contraction; a sensor to detect heart rate or provide other cardiac data; a sensor to detect glucose; or any sensor to detect any other desired physiological characteristic.

A seventh aspect of the invention provides a conductive circuit, garment, garments, or kit according to the earlier aspects of the invention for the use in stimulating muscle activity; detecting muscle stimulation, contraction or relaxation; or treating incontinence, particularly stress incontinence. The circuit, garment or kit may be for regular use, optionally for daily use or for use between 1 and 7 times per week. The circuit, garment, garments or kit may be for use for 15, 20, 25, or 30 minute periods.

An eighth aspect of the invention provides a method of stimulating muscle activity; detecting muscle stimulation, contraction or relaxation; comprising the step of applying a conductive circuit, garment or kit according to any of the earlier aspects of the invention to the human or animal body.

A ninth aspect of the invention provides a method of treating incontinence, particularly stress incontinence; comprising the step of applying a conductive circuit, garment or kit according to any of the earlier aspects of the invention to the human or animal body.

In such a method the conductive circuit, garment or kit may be applied to the hips, thighs and/or buttocks of the human body.

Also provided is a method of stimulating muscle activity; detecting muscle stimulation, contraction or relaxation; or treating incontinence, particularly stress incontinence, comprising delivering electric current to a patient using a conductive circuit, garment or kit of the invention.

Throughout the description and claims of this specification, the words "comprise" and "contain" and variations of the words, for example "comprising" and "comprises", mean "including but not limited to", and do not exclude other components, integers or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible.

BRIEF DESCRIPTION OF THE DRAWINGS

One or more embodiments of the invention will now be described, by way of example only, with reference to the accompanying drawings, in which.

DETAILED DESCRIPTION

Figure 1:
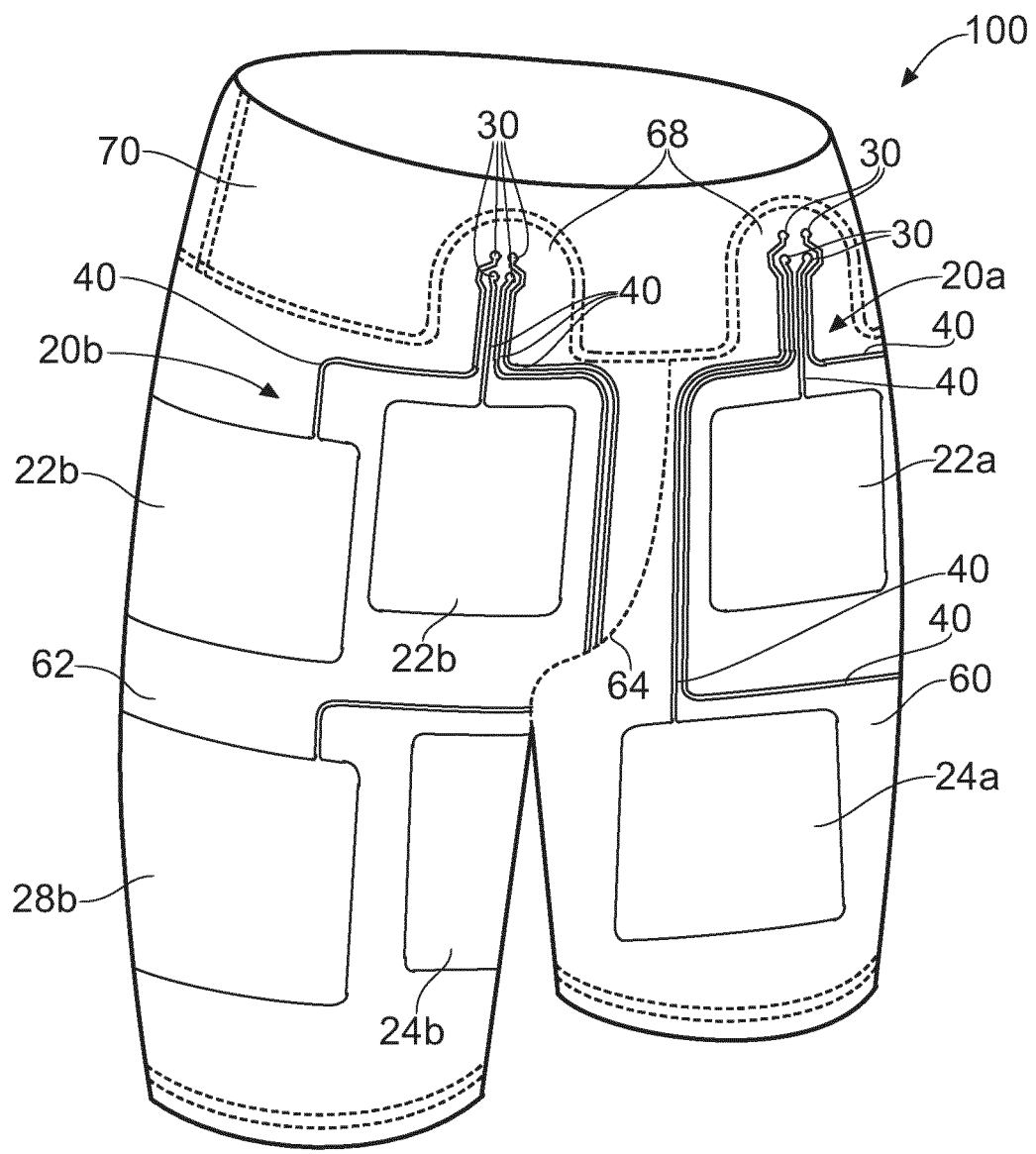
FIG. 1 is a perspective view of a garment according to an embodiment of the invention, showing a conductive circuit printed on an inside surface thereof.
Figure 2:
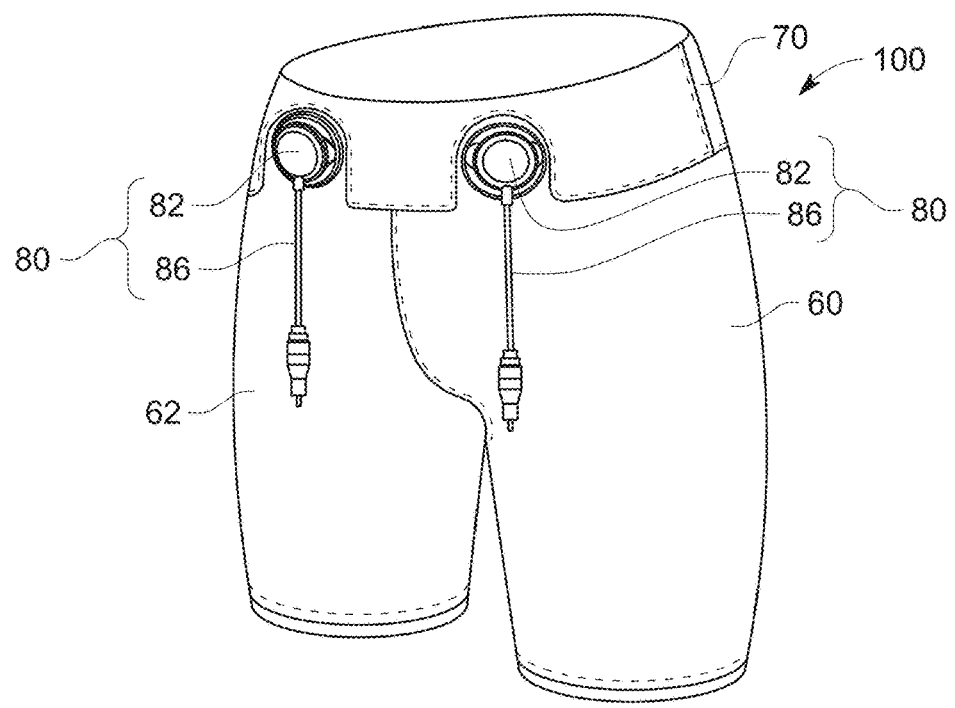
FIG. 2 is a perspective view of a garment according to an embodiment of the invention, with electrical connectors and cables attached thereto.
Figure 3:
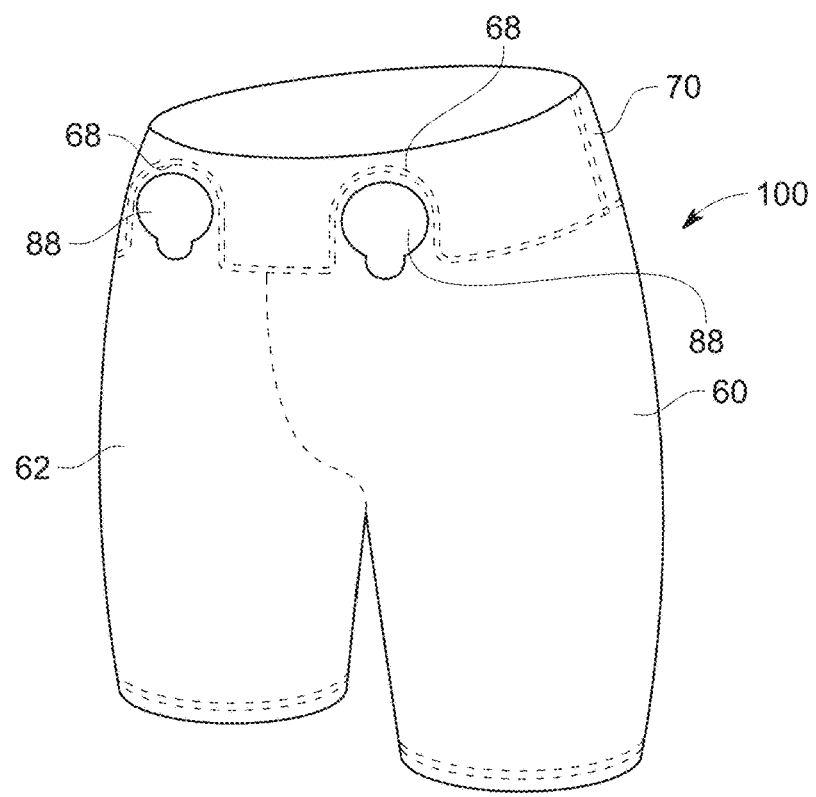
FIG. 3 is a perspective view of the garment of FIG. 2 with electrical connectors and cables omitted.
Figure 4:
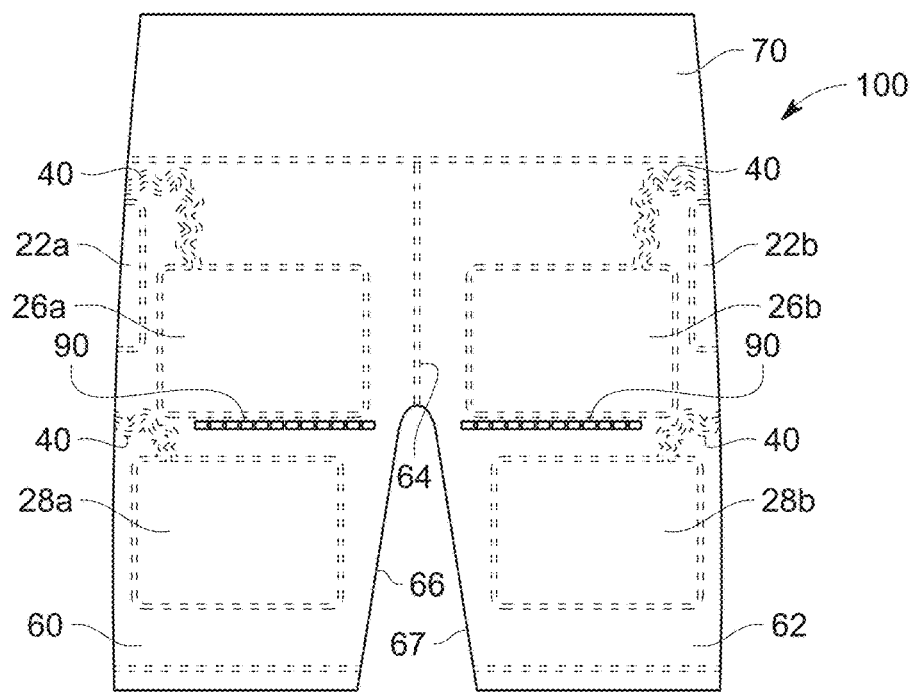
FIG. 4 is a rear view of the garment of FIG. 2, showing a conductive circuit printed on an inside surface thereof.
Figure 5:
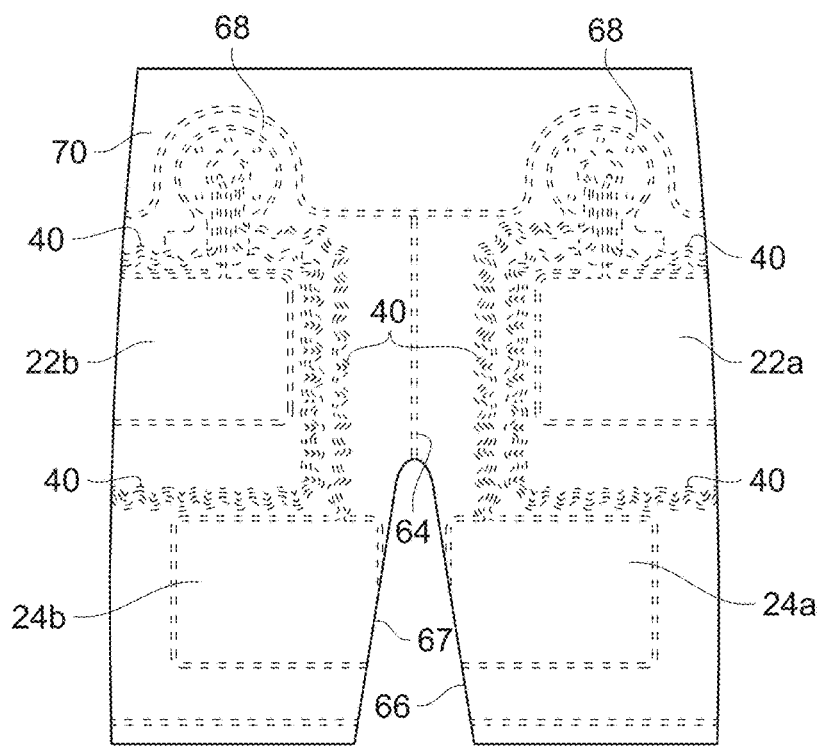
FIG. 5 is a front view of the garment of FIG. 2, showing a conductive circuit printed on an inside surface thereof.
Figure 6:
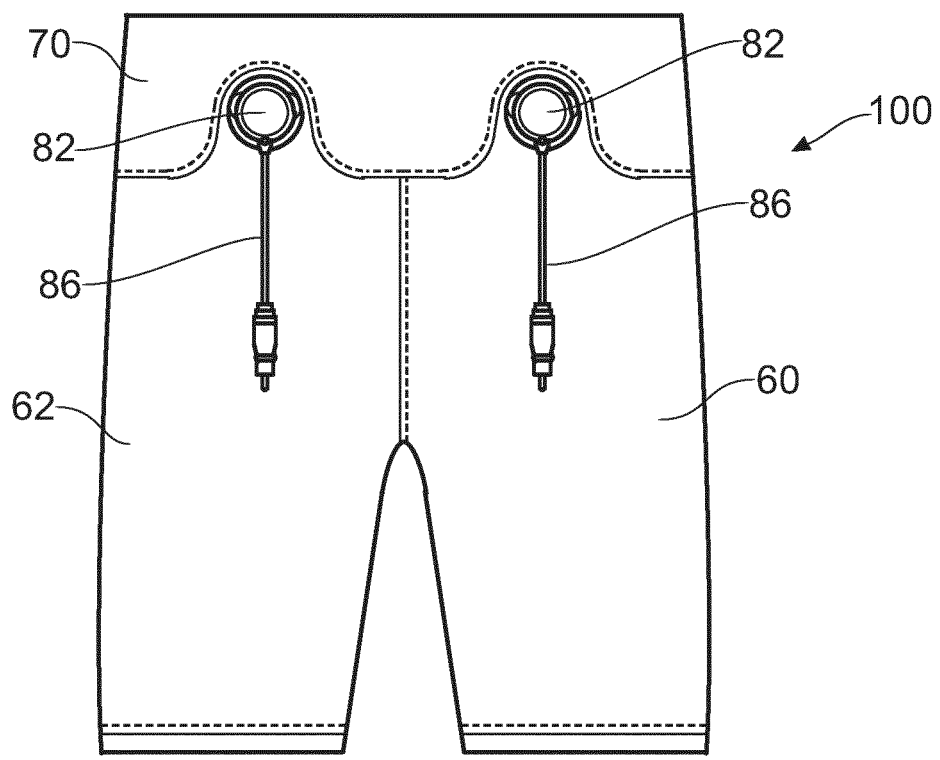
FIG. 6 is a front view of the garment of FIG. 2.
Figure 7:
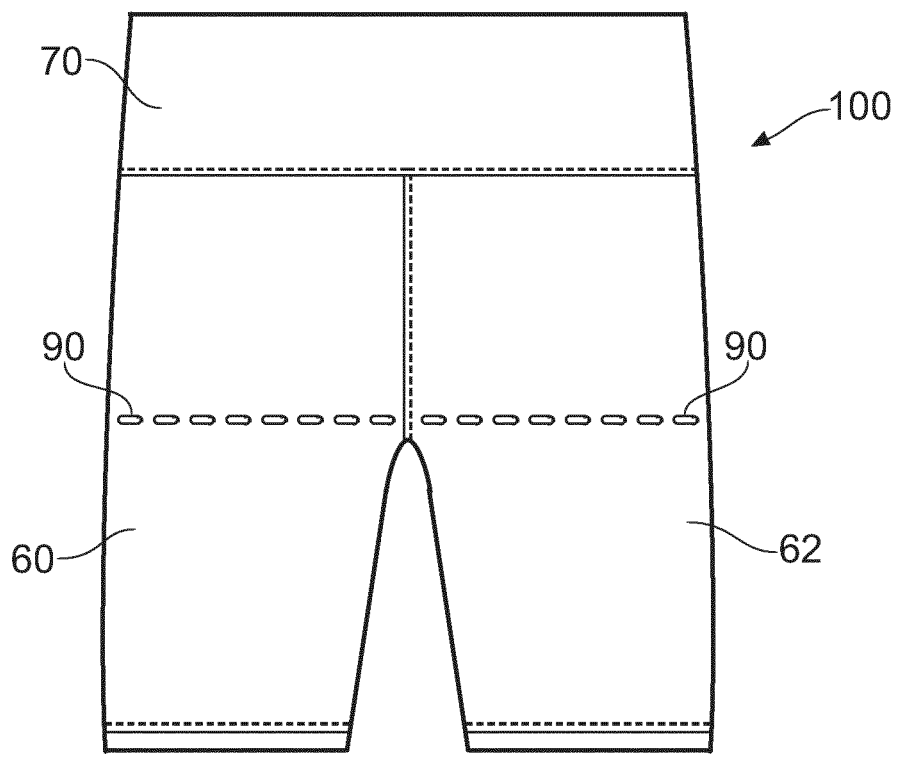
FIG. 7 is a rear view of the garment of FIG. 2.

The invention provides a conductive circuit which may be applied to a garment, for example a garment for the stimulation of pelvic floor muscles. In the embodiments illustrated in FIGS. 1 to 7 the garment comprises a pair of shorts 100. The shorts 100 are made from stretch fabric comprising a polyamide and are designed to fit closely to the body. The shorts are provided with two legs and a waistband area.

The shorts 100 comprise left and right conductive circuits 20 *a*, 20 *b*. The left conductive circuit 20 *a* is provided in a left leg panel 60 of the shorts 100 and the right conductive circuit 20 *b* is provided in a right leg panel 62 of the shorts 100. The left leg and right leg panels 60, 62 are joined together by a crotch seam 64 that extends from a rear portion of the waistband 70 to a front portion of the waistband 70, and left and right inner leg seams, 66, 67. There are no further seams joining the left leg and right leg panels 60, 62 that extend generally or substantially vertically. In this way, each conductive circuit 20 *a*, 20 *b* is contained within a single panel of fabric, and neither conductive circuit 20 *a*, 20 *b* crosses a seam of the shorts 100.

Each conductive circuit 20*a*, 20*b* comprises four electrodes 22, 24, 26, 28 comprising areas of the circuit in which a conductive area of the circuit is arranged to contact the skin of a wearer. The electrodes 22, 24, 26, 28 are each electrically connected to a respective one of eight electrical contact points 30 by a respective conductive track 40. Thus, four of the electrical contact points 30 comprise part of the left conductive circuit 20*a*, and the remaining four electrical contact points 30 comprise part of the right conductive circuit 20*b*.

The four electrical contact points 30 for each conductive circuit 20*a*, 20*b* are each clustered together towards the top of the respective leg panel 60, 62 in the region of the waistband 70. In the illustrated embodiments each leg panel 60, 62 comprises a tab portion 68 that, when assembled into the shorts 100, extends into the waistband area. Each tab portion 68 carries the respective cluster of electrical contact points 30 for a respective one of the conductive circuits 20*a*, 20*b*. In this way, connection to the controller (not shown) via the connecting apparatus (described below) can be achieved in the waistband area, which has been found to be particularly comfortable for users. Moreover, the tab portions 68 comprise a unitary part of each leg panel 60, 62, thereby avoiding the need for any seams crossing the conductive circuits 20a, 20b; seams have been found to adversely affect the electrical resistance of the circuit.

Each electrode is positioned relative to the shorts 100, and in particular relative to its respective leg panel 60, 62, so that it is in contact with a specific region of a user's body when worn. The electrodes 22, 24, 26, 28 are generally located so that they are in contact with the user's skin in the region of the pelvis, to thereby apply a muscular stimulation current which flows laterally across the midline of the user through the user's pelvic floor. That is, current is passed across the pelvis from one leg/hip region to the other via the pelvic floor. Thus, each leg of the shorts is provided with four conductive areas, arranged to contact the skin on the thighs and buttocks of a user when the shorts are worn. The eight conductive areas thus together provide four electrodes for each leg of the shorts.

In alternative embodiments a plurality of the electrodes 22, 24, 26, 28 may be provided as discrete conductive areas exposed within a single region of encapsulating non-conductive material. For example, in such alternative embodiments one electrode may be provided with three conductive areas for providing electrical connections to three discrete areas of a user's skin, and a separate electrode may comprise one such conductive area.

In the illustrated embodiments the first pair of electrodes 22a, 22b (the 'hip electrodes' 22) are located in the region of a user's hip, the second pair of electrodes 24a, 24b are located generally in the region of a user's upper anterior (front) thigh, the third pair of electrodes 26a, 26b (the 'gluteal electrodes' 26) are located generally in the region of the user's buttock, and the fourth pair of electrodes 28a, 28b are located generally in the region of the user's upper posterior (rear) thigh. A visual line 90 is provided on each of the left and right leg panels 60, 62 to provide the user with a visual guide to help ensure correct location of the electrodes 22, 24, 26, 28. The visual line 90 should be aligned with the gluteal crease (also referred to as the gluteal sulcus or gluteal fold) that divides the buttocks from the posterior upper thigh.

The correct positioning of each of the electrodes to ensure effective therapy has been found to be very important. In particular, the inventors have determined that it is especially important to carefully position the gluteal electrodes 26 relative to specific anatomical features. Through experimental analysis, they have established that one or more of (preferably all of) the following positional rules for each of the gluteal electrodes 26 should be adhered to in order to provide optimally effective therapy.

The horizontal position of the gluteal electrodes 26 should be controlled as follows:
A horizontal offset between the inter-gluteal cleft of a wearer of the garment 100 and a nearest side edge of the gluteal electrode of about between 12 mm and 20 mm, optionally about 17 or 18 mm, e.g. 17.5 mm; and/or
A horizontal offset between nearest side edges of the pair of gluteal electrodes at their closest points of between 30 mm and 40 mm, optionally about 35 mm.

In practice, the above positional rules are satisfied by positioning the gluteal electrodes 26 on the garment 100 such that each nearest side edge of each gluteal electrode is horizontally offset from a feature that aligns with the inter-gluteal cleft of a wearer in use by about between 12 mm and 20 mm, optionally about 17 or 18 mm, e.g. about 17.5 mm. For example, such a feature may comprise a line at the rear of the garment 100 bisecting left and right portions of the garment 100 (e.g. rear seam 64).

Similarly, the vertical position of the gluteal electrodes 26 should be controlled as follows:
vertical offset between the natural waist of a wearer of the garment 100 and an uppermost (nearest) edge of the gluteal electrode of at least 75 mm, optionally at least 70 mm; and/or
An uppermost edge of the gluteal electrodes 26 should be lower than an uppermost edge of the hip electrodes 22.

In practice, the above positional rules can be satisfied by positioning the gluteal electrodes 26 on the garment 100 such that each uppermost edge thereof is vertically offset from a feature of the garment 100 that aligns with the user's natural waist in use by at least 70 mm, optionally at least 75 mm.

In some embodiments it may be preferable to instead vertically locate the gluteal electrodes 26 relative to the point of hip of a wearer, i.e. the anterior bony protuberance that can usually be felt beneath the skin and may sometimes be referred to as the anterior superior iliac spine. In such embodiments the uppermost edge of each gluteal electrode 26 should be no more than 25 mm above the point of hip.

References to 'edges' in reference to these positional rules are references to edges of active regions of the respective electrode, i.e. edges of exposed regions in which the conductive material is exposed to contact the skin of a wearer during use.

A particular benefit of the above positional rules is in ensuring correct placement of the gluteal electrodes 26 across multiple garment sizes.

A plurality of garments 100 of different sizes to fit wearers of different sizes, each having gluteal electrodes 26 positioned as defined above, were tested by passing an electromagnetic signal through the circuit 20 and using an internal ultrasound device to establish when a pelvic contraction occurred. It was found that a pelvic contraction was reliably achieved, and effective therapy therefore delivered, in each of the garments 100 in which the gluteal electrodes 26 were positioned according to the above positional rules.

In the illustrated embodiments the conductive circuits 20a, 20b are each a mirror image of the other, but in other embodiments the layout of the conductive circuits 20a, 20b could be varied so that they differ from one another. In particular, the route and shape of the tracks 40 may be different on each leg panel 60, 62. In most embodiments it is expected that the position and shape of the left and right electrodes 22, 24, 26, 28 will be mirror images of one another.

In the arrangements illustrated in FIGS. 2-10 the tracks 40 have a generally wavy, or waveform, shape such that the path of each track generally zig-zags between the respective electrode 22, 24, 26, 28 and electrical contact 30. This arrangement has been found to be particularly beneficial because the waveform shape of the tracks 40 allows for the fabric of the leg panel 60, 62 to be stretched during use of the shorts 100 without unduly affecting the electrical resistance provided by the tracks 40. That is, the wavelength and/or amplitude of the waveform can vary to thereby minimise stretching of the one or more conductive layers of the track.

In other arrangements, such as those illustrated in FIG. 1, the tracks have a generally linear shape.

Each conductive circuit 20a, 20b is formed by printing of a series of conductive and non-conductive layers onto the fabric of the shorts (i.e. the fabric of each of the left and right leg panels 60, 62). An appropriate method of printing the conductive circuits 20a, 20b is described in GB2555592A.

The nature of the printed layers depends on the region of the conductive circuit 20a, 20b to be formed. That is, the arrangement of printed layers differs between the regions of the conductive circuit 20a, 20b in which electrical contact between the conductive circuit 20a, 20b and the skin of the user is wanted (i.e. the electrodes 22, 24, 26, 28) and the regions in which electrical contact between the conductive circuit 20a, 20b and the skin of the user is not wanted (i.e. the tracks 40).

In general terms, a series of layers is applied onto the fabric of the shorts to form each conductive circuit. The layers applied are an adhesive layer, an encapsulation layer (non-conductive layer), a layer of conductive ink (conductive layer, which may comprise first and second conductive layers), a further encapsulation layer (non-conductive layer). The further encapsulation layer is provided over areas of the conductive ink that should not be in contact with a user's skin, and leaves areas of exposed conductive ink, as conductive areas (electrodes). The further encapsulation layer comprises first and second non-conductive layers, as described further below.

The conductive circuits 20a, 20b are generally formed by printing a series of conductive and non-conductive ink layers in a desired order onto a substrate (not shown), and then transferring the printed layers from the substrate onto the respective leg panel 60, 62 by a transfer process. For example, the substrate may be placed over the leg panel 60, 62, heat and pressure applied to transfer the printed layers to the leg panel 60, 62, and the substrate subsequently peeled away. In such embodiments the printed layers may include an adhesive layer to facilitate bonding between the printed layers and the leg panel 60, 62. In other embodiments the layers may be printed directly onto the fabric of the leg panel 60, 62.

Appropriate printing methods include, but are not limited to, screen printing, reel-to-reel printing, dot matrix printing, laser printing, cylinder press printing, ink jet printing, flexographic printing, lithographic printing, offset printing, digital printing, gravure printing or xerographic printing.

In the illustrated embodiments the tracks 40 each comprise one or more layers of non-conductive material directly adjacent the fabric of the respective leg panel 60, 62, one or more layers of conductive material laminated over the one or more first layers of non-conductive material, and first and second layers of non-conductive material laminated over the one or more layers of conductive material. Each of the layers of non-conductive material is wider than the one or more layers of conductive material so that the layers of conductive material are encapsulated between the non-conductive layers. In this way, the one or more layers of conductive material can provide an electrical connection between the electrodes 22, 24, 26, 28 and the controller, via the connecting apparatus 80, while preventing any direct electrical connection between the tracks 40 and the skin of the user.

The electrodes 22, 24, 26, 28 each comprise one or more layers of non-conductive material directly adjacent the fabric of the respective leg panel 60, 62, and one or more layers of conductive material laminated over the one or more layers of non-conductive material. The one or more layers of non-conductive material act to electrically isolate the layers of conductive material from the fabric. In this way, direct electrical connection between the electrodes 22, 24, 26, 28 and the skin of the user is possible by way of the direct contact between the user's skin and the conductive material only. By forming the electrodes with printed layers in this way, stretching of the fabric in the region of each electrode is minimised, which is advantageous since this prevents undesirable increases in electrical resistance in the electrodes. First and second layers of non-conductive material are laminated around the peripheral edges of the layers of conductive material of each electrode only. This serves to both further prevent stretching of the fabric in the region of the electrodes, and to protect the peripheral edges of the layers of conductive material from damage by peeling or fretting.

The one or more layers of conductive material of each electrode 22, 24, 26, 28 are contiguous with the one or more layers of conductive material of a respective one of the tracks 40 to thereby permit transfer of an electrical signal from the controller to each electrode 22, 24, 26, 28 via the one or more layers of conductive material.

Similarly, the one or more layers of non-conductive material directly adjacent the fabric of each electrode 22, 24, 26, 28 are contiguous with the one or more layers of non-conductive material directly adjacent the fabric of a respective one of the tracks 40. Likewise, the first and layers of non-conductive material of each electrode 22, 24, 26, 28 are contiguous with the first and second layers of non-conductive material of a respective one of the tracks 40.

FIGS. 8A-C and 9A-C illustrate a conductive circuit 20 according to embodiments of the invention that are suitable for use in the shorts 100 of FIGS. 1-7. The circuit 20 illustrated is shown in a form 20a suitable for a left leg panel 30 of the shorts 100, but can equally be applied in mirror image to provide a form 20b suitable for a right leg panel 62 of the shorts 100.

Figure 8A:
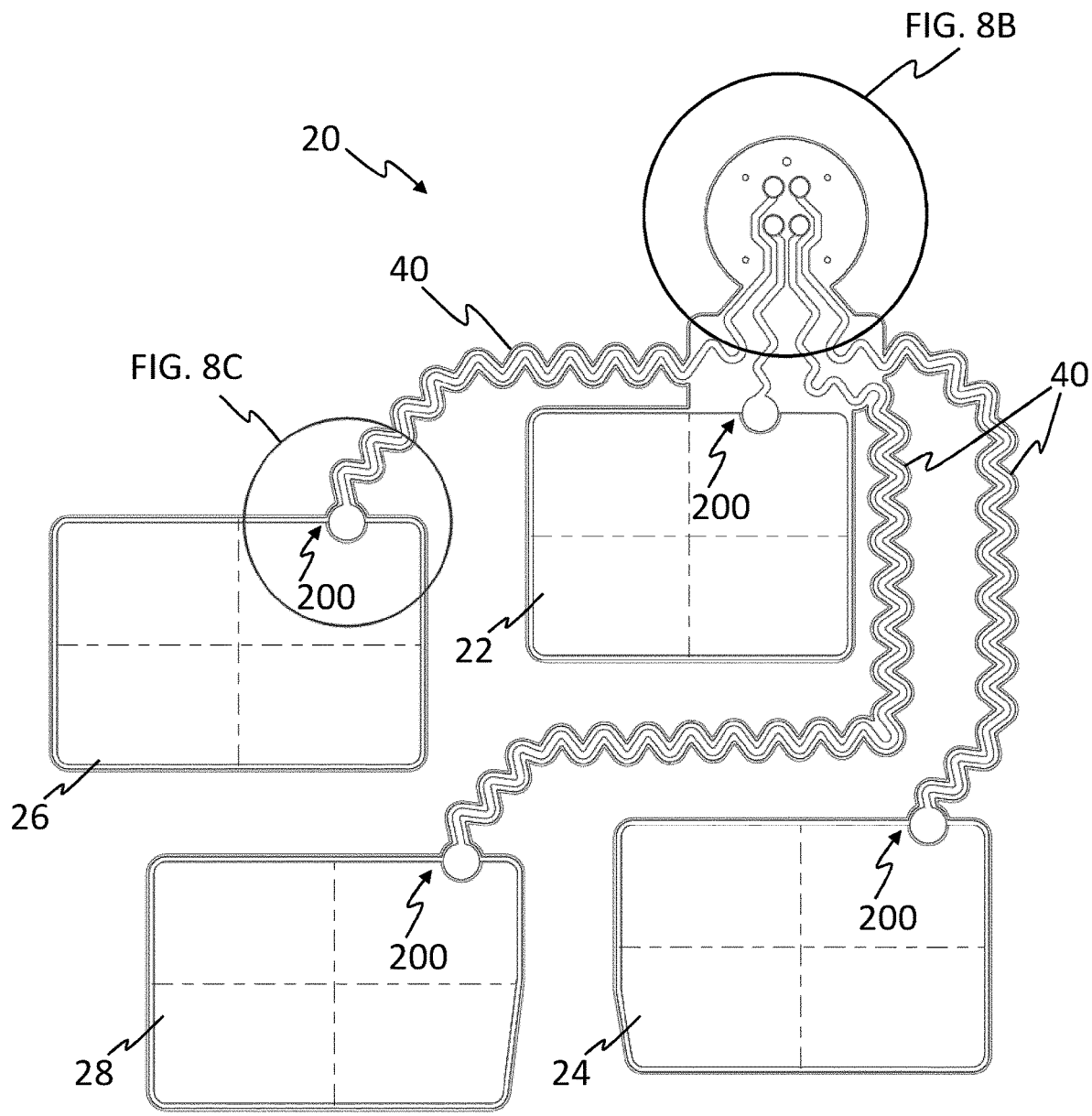
FIGS. 8A, 8B and 8C provide a plan view (FIG. 8A) showing outlines of each of the layers of a conductive circuit according to an embodiment of the invention that is suitable for use in the garment of FIGS. 1 to 7, and detail views thereof (FIGS. 8B and 8C)
Figure 8B:
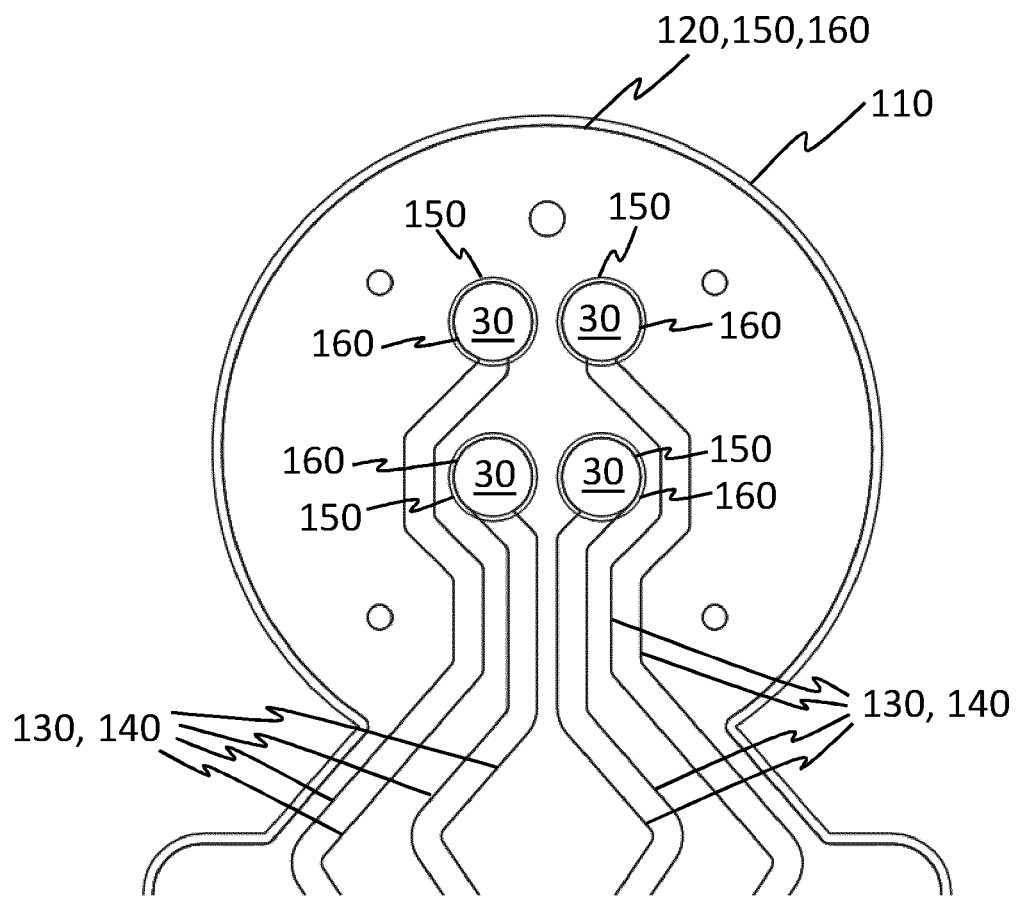
Figure 8C:
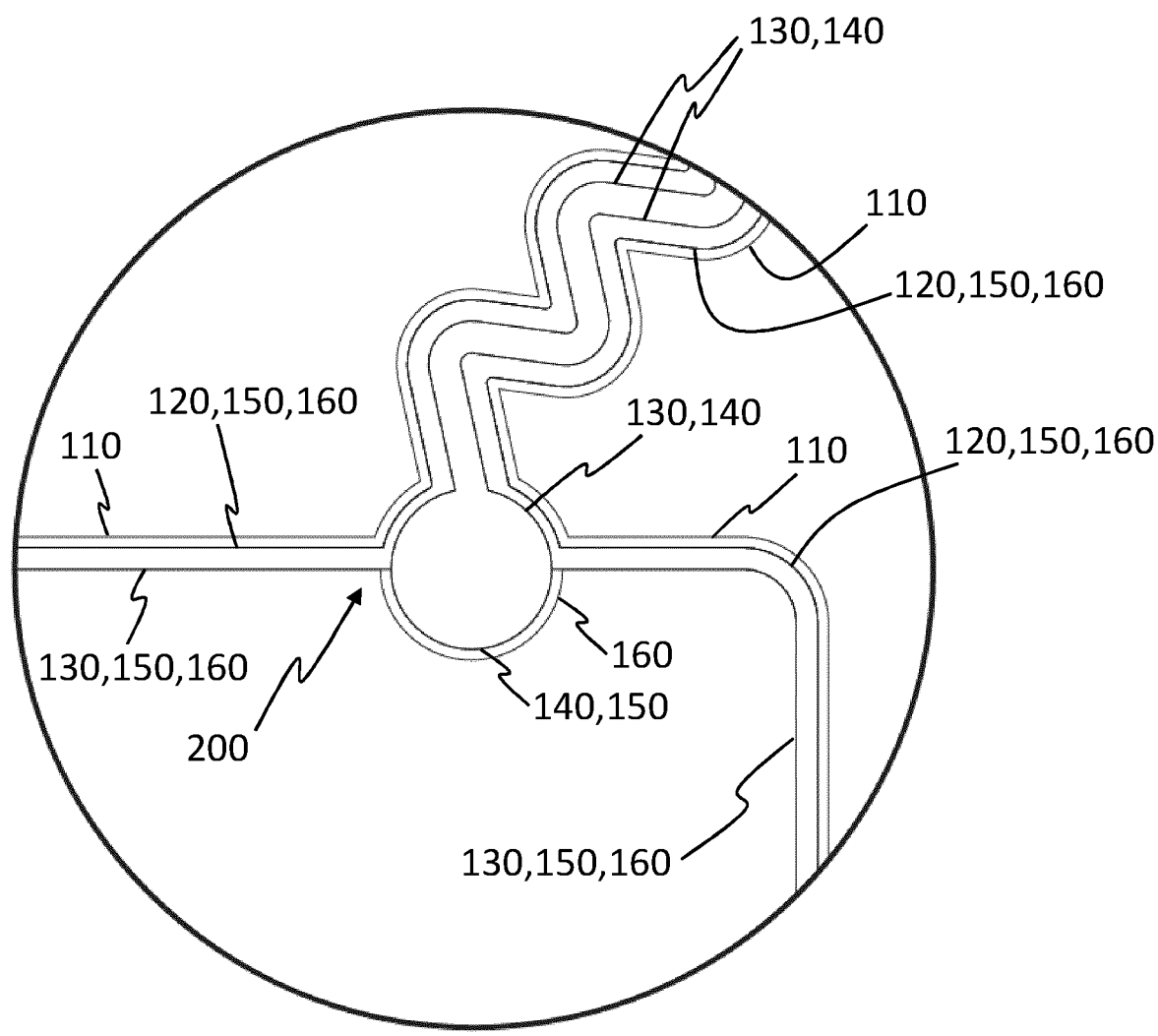
Figure 9A:
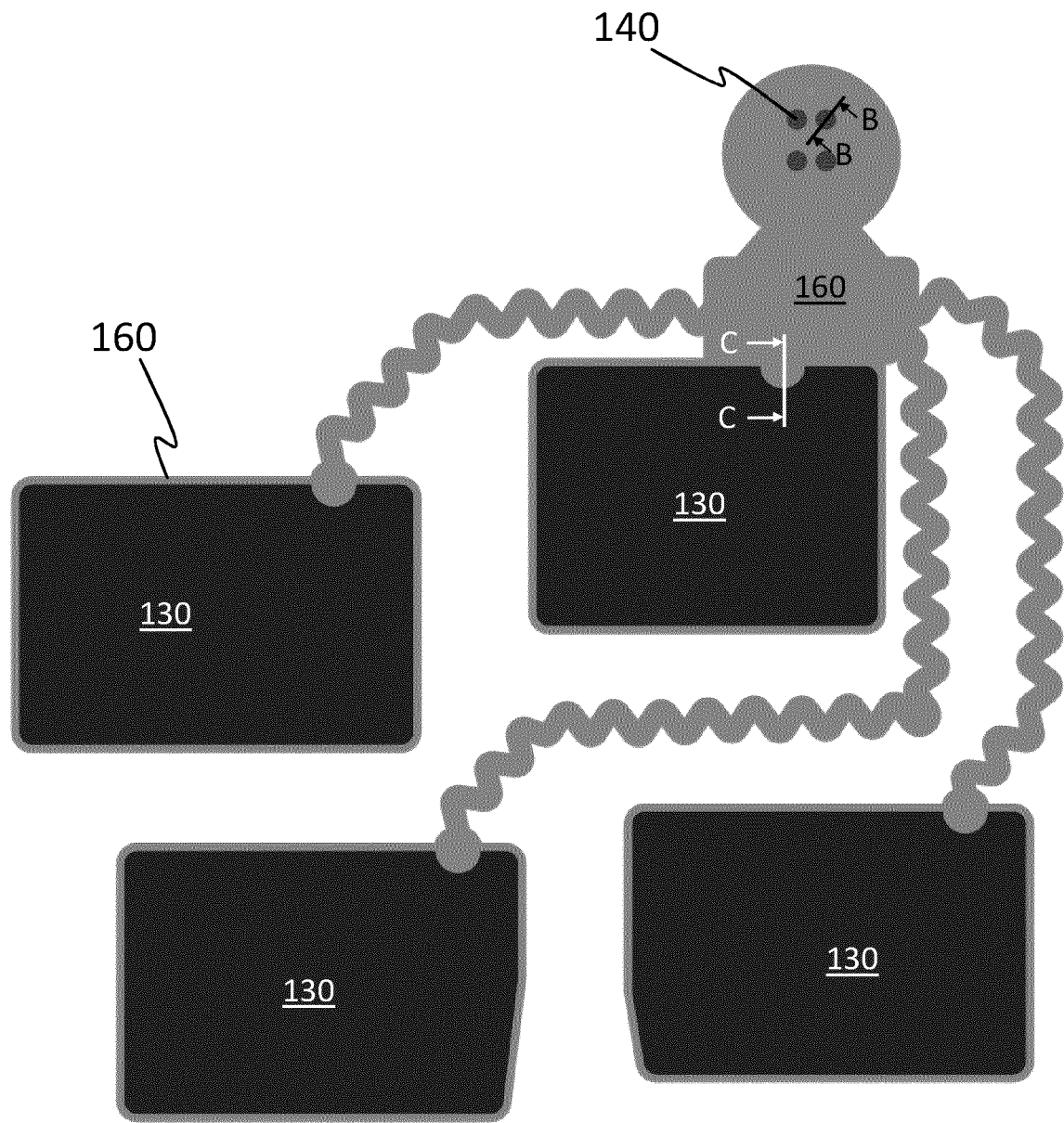
FIGS. 9A, 9B and 9C provide a plan view (FIG. 9A) of the conductive circuit of FIGS. 8A-C in which only surface visible layers are shown, and schematic section views thereof taken along line B-B (FIG. 9B) and line C-C (FIG. 9C)

FIGS. 8A-C shows the outlines of the various layers within the circuit 20, while FIG. 9A shows the visible extent of the layers at the skin-facing side of the circuit 20. The various layers are shown in cross-section in FIGS. 9B and 9C, although it is to be noted that these drawings are purely schematic in nature, not to scale, and not intended to provide a true representation of the geometry of the layers but instead an indication of their ordering and extent.

In general, the circuit 20 is formed from the following layers:

An optional adhesive layer 110 for adhering the circuit 20 to a base, such as a stretch fabric;

One or more (two in the illustrated examples) base non-conductive layers 120 directly adjacent to the adhesive layer, for isolating the circuit 20 from the base;

One or more (two in the illustrated examples) track-and-electrode conductive layers 130 directly adjacent to the base non-conductive layers 120, which form the electrodes 22, 24, 26, 28 and the tracks 40;

One or more (one in the illustrated examples) optional track-only conductive layers 140 directly adjacent to the track-and-electrode conductive layers 130, which are provided throughout the tracks 40 only;

A first encapsulating non-conductive layer 150 directly adjacent to the conductive layers 130, 140, which encapsulates the tracks 40 and the peripheral edges of the electrodes 22, 24, 26, 28, but does not encapsulate the contacts 30; and A second encapsulating non-conductive layer 160 directly laminated with the first encapsulating non-conductive layer 150, which encapsulates the tracks 40 and the peripheral edges of the electrodes 22, 24, 26, 28, but does not encapsulate the contacts 30.

The second encapsulating non-conductive layer 160 has a peripheral outline that corresponds generally to that of the first encapsulating non-conductive layer, with the exception that at the contacts 30 and at the interface 200 between each track 40 and its respective electrode 22, 24, 26, 28 the second encapsulating non-conductive layer 160 overhangs the first encapsulating non-conductive layer 170. In the illustrated examples the overhang provides an offset between a second perimeter edge of the second encapsulating non-conductive layer 160 and a first perimeter edge of the first encapsulating non-conductive layer 150 of about 1 mm.

Figure 9B:
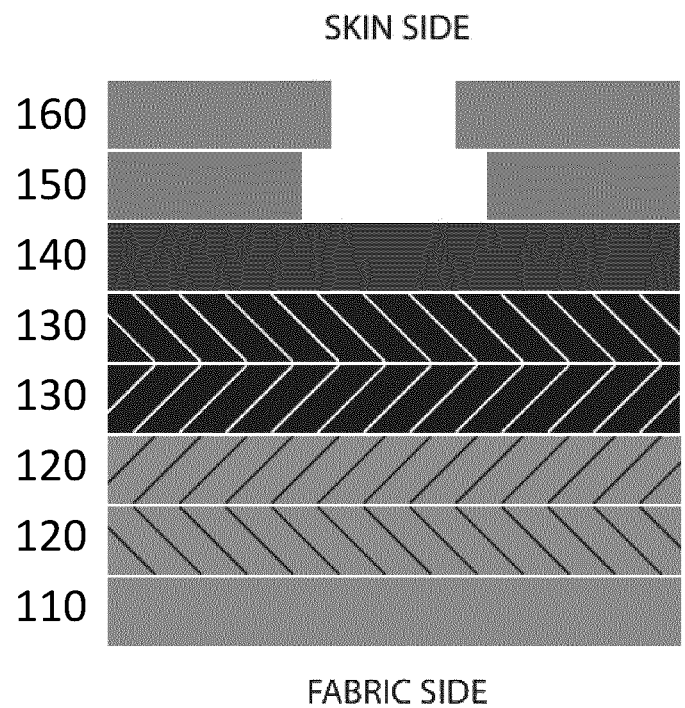

FIGS. 8B and 9B illustrate the arrangement of layers in the conductive circuit 20 at each of the four (in the illustrated examples) contacts 30. Note that FIG. 9B is schematic and not to scale. The skilled reader will understand that overhanging portions of layers will generally conform to the topography of the layers underneath, and will not remain straight and unyielding as illustrated.

Each contact 30 comprises an exposed region of the one or more conductive layers 130, 140. In the illustrated examples it is the one or more track-only conductive layers 140 which are exposed, but in other embodiments any conductive layer may be exposed to form the contacts 30.

The peripheral edge of each contact 30 is defined by a second perimeter edge of the second encapsulating non-conductive layer 160, the second perimeter edge forming a circle. The second perimeter edge is offset from a first perimeter edge of the first encapsulating non-conductive layer 150 so that the second encapsulating non-conductive layer 160 overhangs the first encapsulating non-conductive layer 150. The first perimeter edge thus also forms a circle that is concentric with the circle second perimeter edge, but having a larger diameter. In the illustrated examples the offset, or overhang, is approximately 1 mm. This corresponds to more than 60 times a thickness of the first encapsulating non-conductive layer 150.

By offsetting the second and first perimeter edges of the first and second encapsulating non-conductive layers 150, 160 in this way, so that the second layer overhangs the first layer, load concentrations around the peripheral edge of the contacts 30 are reduced, and the risk of in-service peeling of the first and second encapsulating non-conductive layers 150, 160 away from the conductive layer is minimised.

Figure 9C:
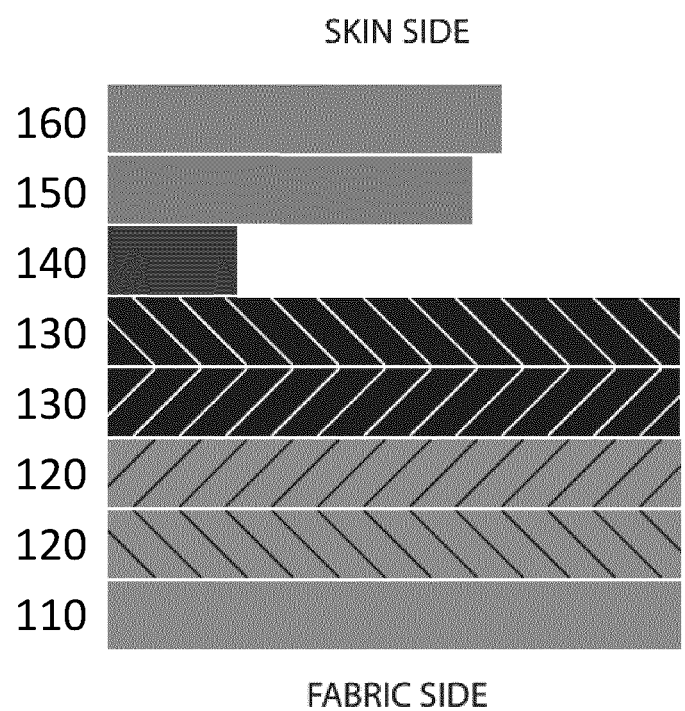

FIGS. 8C and 9C illustrate the arrangement of layers in the conductive circuit around each of the four (in the illustrated examples) interfaces 200 between the tracks 40 and the electrodes 22, 24, 26, 28. Note that FIG. 9C is schematic and not to scale. The skilled reader will understand that overhanging portions of layers will conform to the topography of the layers underneath, and will not remain straight and unyielding as illustrated.

Each electrode 22, 24, 26, 28 comprises an exposed region of the one or more conductive layers 130, 140. In the illustrated examples it is the one or more track-and-electrode conductive layers 130 which are exposed, but in other examples any conductive layer may be exposed to form the electrodes 22, 24, 26, 28.

The first and second encapsulating non-conductive layers 150, 160 terminate at first and second perimeter edges, respectively, adjacent to, but offset from, each interface 200 between track 40 and electrode 22, 24, 26, 28. The track-only conductive layer 140 (where present) also terminates at a perimeter edge adjacent to, but offset from, each interface 200. The perimeter edge of the track-only conductive layer 140 (where present) is coincident with the first perimeter edge of the first encapsulating non-conductive layer 150.

Each of the first and second perimeter edges of the first and second encapsulating non-conductive layers 150, 160 and the perimeter edge of the track-only conductive layer 140 (where present) has a generally arcuate shape such that each layer comprises a generally semi-circular shaped projection 210 that extends from each track 40 beyond the interface 200 and over a portion of the respective electrode 22, 24, 26, 28 (i.e. over a portion of the track-and-electrode conductive layer 130 that is exposed to provide the respective electrode).

The second perimeter edge of the second encapsulating non-conductive layer 160 is offset from the first perimeter edge of the first encapsulating non-conductive layer 150 such that the second encapsulating non-conductive layer 160 overhangs the first encapsulating non-conductive layer 150. In the illustrated examples the offset, or overhang, is approximately 1 mm. This corresponds to more than 60 times a thickness of the first encapsulating non-conductive layer 150.

The interfaces 200 each comprise regions in which a relatively large cross-sectional area of printed layers in the electrode, where the modulus of elasticity is relatively high, meets a relatively small cross-sectional area of printed layers in the track, where the modulus of elasticity is relatively low. These regions can therefore comprise areas of weakness where high loads are concentrated. By offsetting the perimeter edges of the first and second encapsulating non-conductive layers 150, 160 from the interfaces 200, such load concentrations are reduced. Moreover, by offsetting the second and first perimeter edges of the first and second encapsulating non-conductive layers 150, 160, so that the second layer overhangs the first layer, load concentrations are further reduced and the risk of in-service peeling of the first and second encapsulating non-conductive layers 150, 160 is minimised.

Figures 10A, 10B:
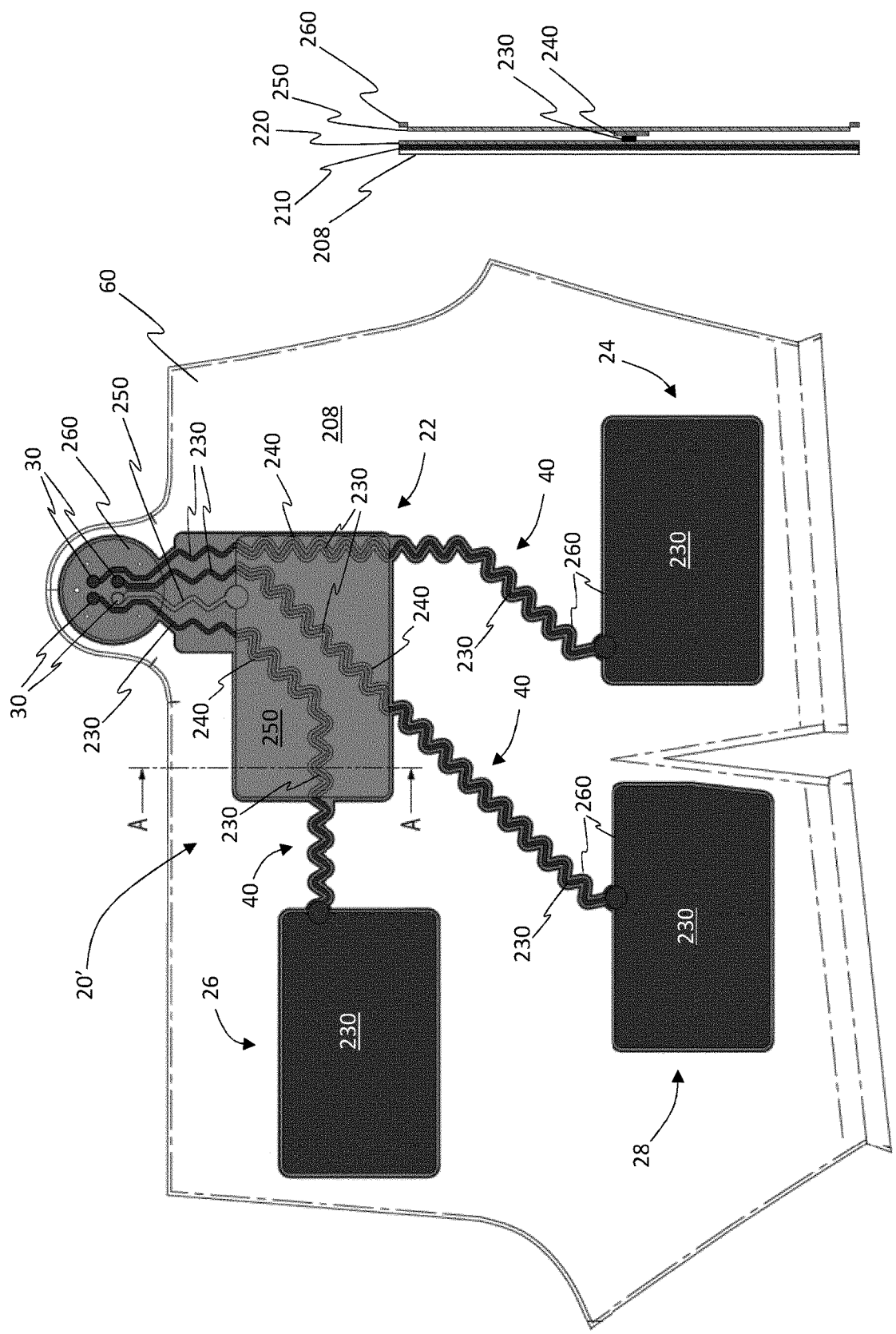
FIGS. 10A and 10B provide a plan view (FIG. 10A) showing outlines of each of the layers of a conductive circuit according to an embodiment of the invention that is suitable for use in the garment of FIGS. 1 to 7, and a schematic section view thereof taken along line A-A (FIG. 10B).

FIGS. 10A and 10B illustrate a further conductive circuit 20' according to embodiments of the invention that is applied to a left leg panel 60 suitable for making up the shorts 100 of FIGS. 1-7. The circuit 20' illustrated is shown in a form 20a suitable for a left leg panel 60 of the shorts 100, but can equally be applied in mirror image to provide a form 20b suitable for a right leg panel 62 of the shorts 100. The circuit 20' is formed by printing the plurality of printed layers, via any of the various processes described herein.

FIG. 10A shows the outlines of the various layers within the circuit 20', with the layers closest to the skin of a wearer shown uppermost in the figure. The outermost non-conductive layer 260 is shown in semi-transparent form throughout, and the hip electrode conductive layer 250 of the hip electrode 22 is also shown in semi-transparent form; this is purely to enable the path of the tracks 40 to be clearly seen.

The various layers are shown in cross-section in FIG. 10B, although it is to be noted that this drawing is purely schematic in nature, not to scale, and not intended to provide a true representation of the geometry of the layers but instead an indication of their ordering and extent. In particular, the skilled reader will understand that overhanging portions of layers will conform to the topography of the layers underneath, and will not remain straight and unyielding as illustrated.

In general, the circuit 20' is formed from the following layers:
  An optional adhesive layer 210 for adhering the circuit 20' to a base, such as a stretch fabric 208 of the panel 60;
  One or more (one in the illustrated examples) base non-conductive layers 220 directly adjacent to the adhesive layer, for isolating the circuit 20' from the base;

One or more (one in the illustrated examples) track-and-electrode conductive layers 230 directly adjacent to the base non-conductive layers 220, which form the tracks 40 and the electrodes 24, 26, 28 other than the hip electrode 22;

One or more (two in the illustrated examples) electrode isolating non-conductive layers 240, which encapsulates and electrically isolates the tracks 40 where they coincide with (overlap with) the hip electrode 22 only;

One or more (one in the illustrated examples) hip electrode conductive layers 250, which form the hip electrode 22 only; and One or more (two in the illustrated examples) outermost encapsulating non-conductive layers 260 directly laminated with the one or more track-and-electrode conductive layers 230 and one or more hip electrode conductive layers 250, which encapsulates the tracks 40 and the peripheral edges of the electrodes 22, 24, 26, 28, but does not encapsulate the contacts 30 or the exposed regions of the electrodes.

A key difference between the conductive circuit 20' of FIGS. 10A and 10B and the conductive circuit 20 of FIGS. 8A-C and 9A-C is that in the conductive circuit 20' the layers of the tracks 40 pass between the hip electrode conductive layer(s) 250 of the hip electrode 22 and the base non-conductive layer(s) 220. That is, the hip electrode 22 overlies, or overlaps with, the tracks 40 that supply an electrical signal to the remaining three electrodes 24, 26, 28.

This arrangement has several features and advantages:

Since the modulus of the fabric is significantly increased in the region of each of the electrodes, the tracks 40 are protected from stretching (and consequential undesirable impact on electrical conductivity) in the region in which they coincide with the hip electrode 22;

The spaces between and adjacent to the electrodes (in particular between the lowermost electrodes 24, 28 and the hip electrode 22, and surrounding the hip electrode 22) have a lower modulus than in the arrangement of FIGS. 8A-C and 9A-C, potentially resulting in a closer fit between the wearer and the electrodes as a result of the increased overall stretchiness of the fabric in those regions; and By minimising the overall length of the tracks 40, the overall amount of conductive material in the circuit 20' is minimised, resulting in a lower overall material cost.

The effect of overlapping the tracks 40 with the hip electrode 22 is achieved by electrically isolating the conductive layer(s) of the hip electrode 22 from the conductive layer(s) of the remaining electrodes 24, 26, 28 and the tracks 40 using the electrode isolating non-conductive layer 240. Thus, the hip electrode 22 is formed from a first conductive layer, and the remaining electrodes 24, 26, 28 and the tracks 40 are formed from a second conductive layer that is electrically isolated from the first conductive layer.

Each contact 30 comprises an exposed region of conductive material. In the illustrated examples the contact 30 associated with the hip electrode 22 comprises an exposed region of the hip electrode conductive layer 250, and each of the remaining contacts 30 comprises an exposed region of the track-and-electrode conductive layer 230.

Similarly, each electrode 22, 24, 26, 28 comprises an exposed region of conductive material. In the illustrated embodiments, each electrode 24, 26, 28 other than the hip electrode 22 comprises an exposed region of track-and-electrode conductive layer 230, and the hip electrode 22 comprises an exposed region of hip electrode conductive layer 250.

In the illustrated embodiments the tracks 40 overlap with the hip electrode 22, but the skilled reader will understand that in other embodiments one or more of the tracks 40 may overlap with any electrode in a conductive circuit formed from a plurality of printed layers.

In all embodiments, the one or more layers of non-conductive material preferably comprise one or more non-conductive ink layers. A suitable printing ink comprises a water based printing ink, an ultraviolet-cured printing ink, a solvent based ink, or a latex printing ink, for example. A particularly preferred ink for the non-conductive layers comprises a screen-printable ink of CMYK toner.

Similarly, the one or more layers of conductive material preferably comprise one or more conductive ink layers. The conductive material may comprise an electrically conductive metal, such as silver, silver chloride, copper or combinations or alloys thereof, or another conductive material such as a carbon-containing material. Suitable conductive inks may be supplied by Engineering Materials Systems, Inc. under the brand name Engineered Conductive Materials (ECM)™.

Each of the layers of conductive or non-conductive material may have a thickness of 0.5 mm or less, 0.4 mm or less, 0.3 mm or less, 0.2 mm or less, 0.1 mm or less, 0.05 mm or less. For example, each of the first and second layers of non-conductive material 150, 160 or the electrode isolating non-conductive layers 240 may be approximately 0.018 mm thick. Similarly, each of the layers of conductive material may be approximately 0.006 mm thick. In the embodiments illustrated in FIGS. 8A-c and 9A-C, for example, three layers of conductive material are provided in the tracks 40 and two layers are provided in the electrodes 22, 24, 26, 28.

Each conductive circuit 20, 20a, 20b, 20' is provided with a connecting apparatus 80 to connect it to a controller (not shown). The controller may be as described in WO2007138071. The connecting apparatus 80 may, for example, be a wire with appropriate connectors. In the illustrated embodiments the connecting apparatus 80 comprises left and right connectors 82 that provide an electrical connection between the conductive circuits 20, 20', 20a, 20b and left and right cables 86.

Each connector 82 comprises a rigid two-part assembly. A first part of each connector 82 is durably fixed to a respective leg panel 60, 62 so that each of four electrical connecting pins within the first part form an electrical connection with a respective one of the four electrical contact points 30 of the respective conductive circuit 20, 20', 20a, 20b. A second part of each connector 82 can be removably connected to the first part to create an electrical connection therebetween. For example, one or both of the first and second parts may comprise magnets to facilitate an easy interconnection. In such embodiments each connector 82 may comprise magnets with opposing polarities to ensure that a user connects the correct first and second parts together, and to prevent incorrect connection. The second part of each connector 82 provides a durable connection to the respective cable 86, which comprises a jack for connection of the shorts 100 with the controller (not shown).

While it is desirable for the fabric of the shorts 100 to be stretchy to enable easy use by users and to ensure a good contact between the user's skin and the electrodes, it has been found that it is desirable to restrict stretch of the fabric in the region of the connectors 82 in order to ensure a reliable electrical connection between the controller and the conductive circuits 20, 20', 20a, 20b. In the illustrated embodiments this has been achieved by means of left and right rubber sheet layers 88 which are each sandwiched between the respective connector 82 and the fabric of the respective leg panel 60, 62. In preferred arrangements the rubber sheet layers 88 (and the fabric of the respective leg panel 60, 62) are each sandwiched between rigid portions of the first part of the respective connector 82. This arrangement not only provides a reliable electrical connection, but also serves to prevent water ingress into the connector 82, for example during washing of the shorts 100.

Electrical connectivity between the electrodes 22, 24, 26, 28 and the user's skin is preferably maximised by use of an electrolytic fluid. For example, the user may spray the electrodes with electrolytic solution or saline solution prior to use.

The invention claimed is:

1. A conductive circuit comprising an electrode for delivering an electromagnetic signal to a human or animal body, the conductive circuit comprising a base and a printed layer supported by the base, the printed layer including:
   a printed conductive layer;
   a first printed non-conductive layer partially overlaid on the printed conductive layer, the first printed non-conductive layer partially defined by a first perimeter edge; and
   a second printed non-conductive layer partially defined by a second perimeter edge and partially overlaying the first printed non-conductive layer, wherein a portion of the second perimeter edge is offset from the first perimeter edge so that the second printed non-conductive layer overhangs the first printed non-conductive layer only at an exposed region of the printed conductive layer wherein the first printed non-conductive layer and the second printed non-conductive layer do not overlay the printed conductive layer.

2. The conductive circuit according to claim 1, wherein the base comprises a stretch fabric.

3. The conductive circuit according to claim 1, wherein the first and second printed non-conductive layers have a higher modulus of elasticity than the base.

4. The conductive circuit according to claim 1, wherein the second perimeter edge defines the exposed region of the conductive circuit.

5. The conductive circuit according to claim 1, wherein the second printed non-conductive layer comprises an outermost layer of the conductive circuit.

6. The conductive circuit according to claim 1, wherein the exposed region is defined at least partially by the second perimeter edge.

7. The conductive circuit according to claim 1, further comprising a connection track providing an electrically conductive path between the electrode and an electrical contact configured to enable connection to a controller adapted to supply an electromagnetic signal to the electrode.

8. The conductive circuit according to claim 7, wherein the first perimeter edge and/or the second perimeter edge are offset from an interface location where the connection track and the electrode meet.

9. The conductive circuit according to claim 8, wherein the interface location where the connection track and the electrode meet comprises a region in which a cross-sectional area of the conductive circuit changes.

10. The conductive circuit according to claim 8, wherein the interface location where the connection track and the electrode meet comprises a region in which a modulus of elasticity of the conductive circuit changes.

11. The conductive circuit according to claim 7, wherein a portion of the printed conductive layer comprises the connection track, the printed conductive layer being electrically connected to electrode.

12. The conductive circuit according to claim 11, wherein the printed conductive layer is a first printed conductive layer to; and wherein the connection track further comprises a second printed conductive layer deposited on the portion of the printed conductive layer comprising the connection track.

13. The conductive circuit according to claim 11, wherein the first and second printed non-conductive layers overlay the portion of the printed conductive layer comprising the connection track to thereby encapsulate at least a majority of the printed conductive layer.

14. The conductive circuit according to claim 13, wherein the electrical contact comprises an exposed region of the portion of the printed conductive layer comprising the connection track in which the printed conductive layer is not overlaid by the first and second printed non-conductive layers, and wherein the exposed region is defined by the second perimeter edge.

15. The conductive circuit according to claim 7, comprising a connector electrically connected to each electrical contact of the connection track and configured to provide an electrical connection between the electrode and a power supply adapted to supply the electromagnetic signal to the electrode or the controller adapted to supply the electromagnetic signal to the electrode.

16. The conductive circuit according to claim 1, wherein the printed layer further comprises a further printed non-conductive layer between the printed conductive layer and the base.

17. A kit of parts for providing a conductive circuit according to claim 1, comprising a base, and a substrate carrying the printed layer, the substrate being configured to enable transfer of the printed layer onto the base by a transfer process to provide the conductive circuit.

18. A wearable garment comprising a conductive circuit according to claim 1, a fabric of the wearable garment forming the base of the conductive circuit.

19. The wearable garment according to claim 18 that is wearable on a lower body region of a human or animal body, the wearable garment comprising two conductive circuits including a first conductive circuit having one an electrode configured to contact a left side of the body and a second conductive circuit having a corresponding electrode configured to contact a right side of the body.

\* \* \* \* \*